United States Patent

Caton et al.

[11] 4,424,374
[45] Jan. 3, 1984

[54] BICYCLOHEPTANE DERIVATIVES

[75] Inventors: Michael P. L. Caton, Upminster; Keith A. J. Stuttle, Rochford, both of England

[73] Assignee: May & Baker Limited, London, England

[21] Appl. No.: 243,567

[22] Filed: Mar. 13, 1981

Related U.S. Application Data

[60] Continuation of Ser. No. 81,841, Oct. 4, 1979, abandoned, which is a division of Ser. No. 27,788, Apr. 6, 1979, abandoned.

[30] Foreign Application Priority Data

Apr. 10, 1978 [GB] United Kingdom ............... 14032/78

[51] Int. Cl.$^3$ ............................................. C07C 61/38
[52] U.S. Cl. .................................... 424/308; 562/466; 556/436; 424/317; 560/118; 560/56; 549/427; 549/501
[58] Field of Search ................. 560/56, 119; 562/466, 562/501; 424/308, 317; 260/345.2, 345.7 R, 347.3, 347.4

[56] References Cited

U.S. PATENT DOCUMENTS 4,308,396 12/1982 Nicolaou et al. .................. 560/118

Primary Examiner—Paul J. Killos
Attorney, Agent, or Firm—Stevens, Davis, Miller & Mosher

[57] ABSTRACT

Compounds of the general formula:

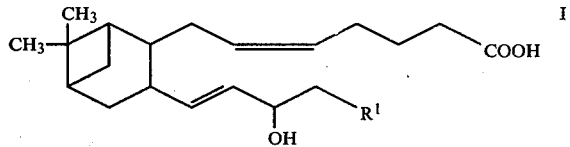

wherein $R^1$ represents a straight- or branched-chain alkyl group containing from 1 to 6 carbon atoms or a phenoxy or benzyl group, and pharmaceutically acceptable salts and esters thereof, possess pharmacological properties of use in the fields of mammalian reproduction and cardiovascular disease.

9 Claims, No Drawings

BICYCLOHEPTANE DERIVATIVES

This is a continuation of application Ser. No. 81,841 filed Oct. 4, 1979 which in turn is a division of application Ser. No. 27,788, filed Apr. 6, 1979, both now abandoned.

DESCRIPTION

This invention relates to new bicycloheptane derivatives, to a process for their preparation, and to compositions containing them.

The present invention provides compounds of the general formula:

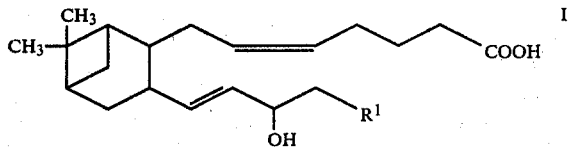

wherein $R^1$ represents a straight- or branched-chain alkyl group containing from 1 to 6 carbon atoms or a phenoxy or benzyl group, and pharmaceutically acceptable salts and esters, preferably alkyl esters containing from 1 to 12 carbon atoms in the alkyl moiety which may be straight- or branched-chain, thereof. $R^1$ preferably represents the n-butyl group.

In formula I the two double bonds are in the cis-configuration and the trans-configuration, as depicted.

As will be appreciated by those skilled in the art, the structure shown in formula I has at least five centres of chirality, two of these centres of chirality being at the ring carbon atoms to which the side chains —CH$_2$—CH=CH—(CH$_2$)$_3$—COOH and —CH=CH—CH(OH)—CH$_2$—R$^1$ are attached, two being at the two bridgehead carbon atoms, and the fifth centre of chirality being at the carbon atom in the hydroxymethylene group depicted. Further centres of chirality may occur in the group $R^1$. The presence of centres of chirality, as is well known, leads to the existence of isomerism. The present invention includes all isomers of general formula I and mixtures thereof.

Especially preferred compounds of the present invention are those which have a configuration such that the side-chains —CH$_2$—CH=CH—(CH$_2$)$_3$—COOH and —CH=CH—CH(OH)—CH$_2$—R$^1$ are attached to the ring in the trans-configuration with respect to each other.

Compounds of the invention which are of especial importance are those of the general formula:

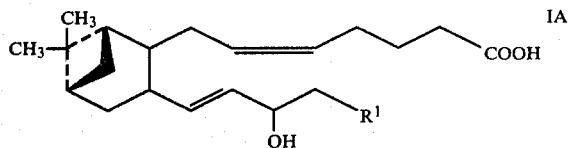

(wherein $R^1$ is as hereinbefore defined), and pharmaceutically acceptable salts and esters thereof and, in particular, those of the general formula:

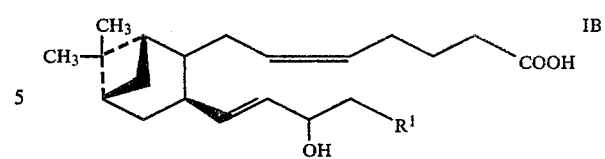

(wherein $R^1$ is as hereinbefore defined) and pharmaceutically acceptable salts and esters thereof.

Compounds of formula I which are of particular importance include 7-{(1S,2R,3R,5S)-3-(3R-hydroxyoct-trans-1-enyl)-6,6-dimethylbicyclo[3,1,1]hept-2-yl}hept-cis-5-enoic acid, and 7-{(1S,2R,3R,5S)-3-(3S-hydroxyoct-trans-1-enyl)-6,6-dimethylbicyclo[3,1,1]hept-2-yl}hept-cis-5-enoic acid, i.e. the compounds of general formula IB wherein $R^1$ represents an n-butyl group.

In the formula drawings in this specification the usual convention will be followed, viz. that dotted lines indicate bonds below the plane of the paper and wedge-shaped lines indicate bonds above the plane of the paper.

The compounds of the present invention possess pharmacological properties which are of utility in medicine and veterinary science; for example they are of use in the field of mammalian reproduction, being useful, e.g. in modifying, qualitatively or quantitatively, or synchronising various functions of female mammalian reproductive systems, and they are also of use in the treatment or prevention of cardiovascular disease.

Compounds of formula I which are of particular importance by virtue of their pharmacological properties include the compound 7-{(1S,2R,3R,5S)-3-[3-(R or S)hydroxyoct-trans-1-enyl]-6,6-dimethylbicyclo[3,1,1]hept-2-yl}hept-cis-5-enoic acid which may be prepared as described hereinafter in Example 1.

For example, in laboratory tests in anaesthetised rats on the 7th to 9th day of pregnancy, this compound was administered by the intravenous route and was found to stimulate uterine contraction. Its activity was compared with that of a standard compound, prostaglandin E$_1$ (PGE$_1$), and was expressed as a ratio. The said compound of formula I was found to be approximately one quarter as active as PGE$_1$ in that test.

After the uterine stimulant effect had worn off, a prolonged inhibition of uterine contraction was observed, during a period between 5 and 30 minutes after administration of the test compound of formula I.

Furthermore, at lower doses, of between one half and one twentieth of the minimum effective uterine stimulant dose, the said compound of formula I caused an immediate, non-dose-related, inhibition of uterine contraction, lasting for a period of up to 5 minutes.

As a feature of the present invention, compounds of formula I are prepared by the acid hydrolysis of compounds of the general formula:

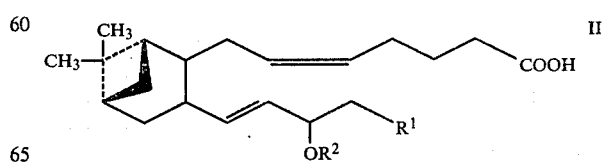

wherein $R^1$ is as hereinbefore defined and $R^2$ represents a suitable acid-labile protecting group.

Hydrolysis of compounds of formula II is generally effected in mild acidic conditions, for example by treatment with an aqueous inorganic acid, e.g. dilute hydrochloric acid or a catalytic quantity of perchloric acid, or an aqueous organic acid, for example aqueous acetic acid, e.g. 50–80% v/v aqueous acetic acid, preferably in the presence of an inert organic solvent, for example a lower alkanol, e.g. ethanol, or an ether, e.g. diethyl ether or tetrahydrofuran, and optionally in the presence of a cation exchange resin, e.g. Dowex $AG_{50}W$-X8 H+ resin. The hydrolysis is generally carried out at temperatures from 0° C. to 100° C.; when dilute hydrochloric acid is used, at from 40° to 80° C., preferably from 50° to 60° C.; when a catalytic quantity of perchloric acid is used, at from 0° C. to 40° C., preferably from 15° to 25° C.; and when aqueous acetic acid is used, at from 0° to 80° C., preferably from 35° to 50° C.

Suitable acid labile protecting groups represented by $R^2$ are those which are easily removed by acid hydrolysis and which do not cause side reactions, e.g. a 2-tetrahydropyranyl group unsubstituted or substituted by at least one straight- or branched-chain alkyl group containing from 1 to 4 carbon atoms, or a 2-tetrahydrofuranyl group, or a tert-butyldiphenylsilyl group, or a trialkylsilyl group of the general formula:

$$-SiR^3R^4R^5 \quad\quad\quad III$$

(wherein $R^3$ and $R^4$, which may be the same or different, each represents a methyl or ethyl group and $R^5$ represents a straight- or branched-chain alkyl group containing from 1 to 4 carbon atoms), e.g. a trimethylsilyl, dimethylisopropylsilyl or tert-butyldimethylsilyl group, or a 1-alkoxyalkyl group of the general formula:

$$-CH(CH_2R^6)OR^7 \quad\quad\quad IV$$

(wherein $R^6$ represents a hydrogen atom or a straight- or branched-chain alkyl group containing from 1 to 4 carbon atoms and $R^7$ represents a straight- or branched-chain alkyl group containing from 1 to 4 carbon atoms) e.g. a 1-ethoxyethyl group.

Preferably $R^2$ represents a 2-tetrahydropyranyl group.

Compounds of formula II may be prepared by the application or adaptation of known methods, for example as shown on the following diagrammatical representation:

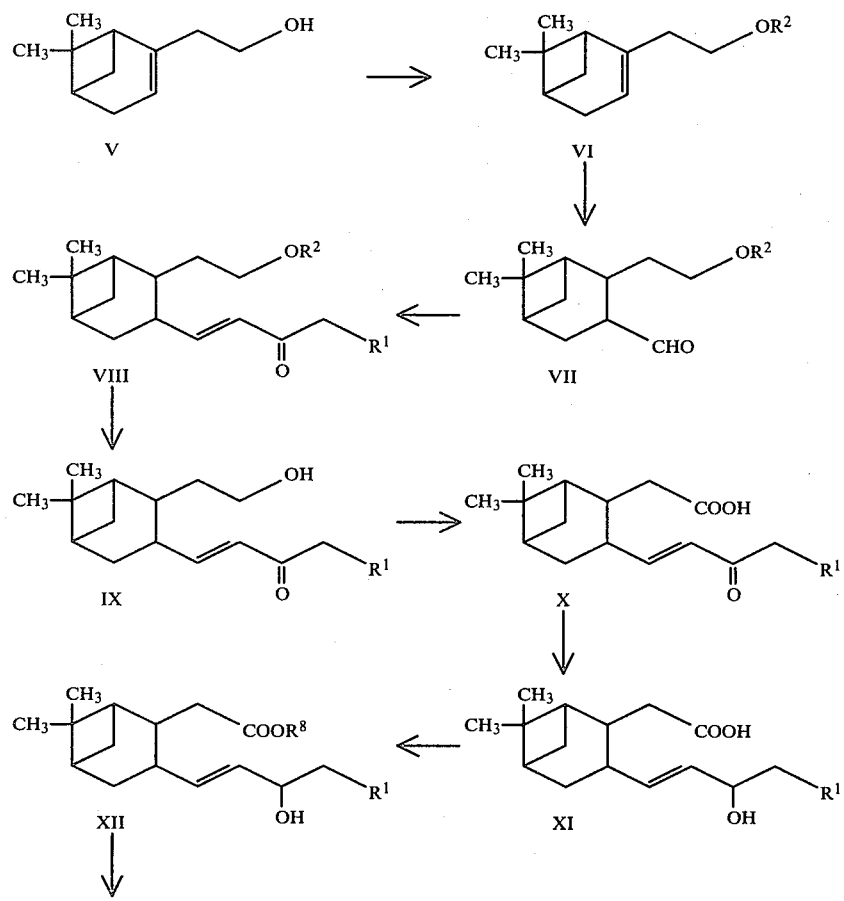

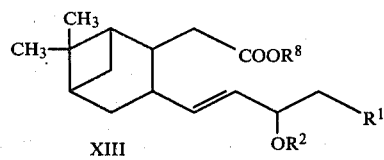
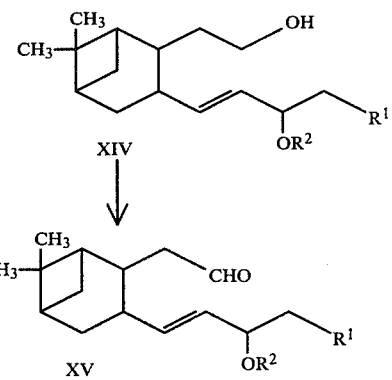

(wherein R¹ and R² are as hereinbefore defined and R⁸ represents an alkyl group preferably containing from 1 to 4 carbon atoms, preferably a methyl group).

By the term "known methods", as used in the present specification, is meant methods heretofore used or described in the literature.

Compounds of general formula V may be prepared by the application or adaptation of known methods. When the eventual product required is a compound of general formula IA, then the starting material of general formula V is the isomer 2-{(1R,5S)-6,6-dimethylbicyclo[3,1,1]hept-2-en-2-yl}ethanol, which is an article of commerce obtainable from the natural product β-pinene.

Compounds of formula II may be prepared from compounds of formula XV by reaction with (4-carboxybutyl)triphenylphosphonium bromide in the presence of a strong base, for example a mixture of dimethyl sulphoxide and sodium hydride or a mixture of tetrahydrofuran and potassium tert-butoxide, and in an inert atmosphere, e.g. nitrogen, followed by acidification.

Compounds of formula XV may be prepared by the oxidation of compounds of formula XIV by reaction with pyridinium chlorochromate in the presence of sodium acetate.

Compounds of formula XIV may be prepared by the reduction of compounds of formula XIII for example by means of lithium aluminium hydride in an ethereal solvent, e.g. tetrahydrofuran.

Compounds of formula XIII may be prepared from compounds of formula XII by the application or adaptation of known methods.

For example, compounds of formula XIII wherein R² represents a 2-tetrahydropyranyl group unsubstituted or substituted by at least one straight- or branched-chain alkyl group containing from 1 to 4 carbon atoms, or a 2-tetrahydrofuranyl group or a 1-alkoxyalkyl group of formula IV (wherein R⁶ and R⁷ are as hereinbefore defined) may be prepared by the reaction of compounds of formula XII with 2,3-dihydropyran or the appropriate alkylated 2,3-dihydropyran, or with 2,3-dihydrofuran or with a compound of the general formula:

$$R^6CH=CHOR^7 \qquad XVI$$

(wherein R⁶ and R⁷ are as hereinbefore defined), e.g. ethyl vinyl ether, in the presence of a catalytic quantity of an acid, for example an inorganic acid (e.g. concentrated hydrochloric acid) or a strong organic acid (e.g. p-toluenesulphonic acid). The reaction is preferably carried out in the presence of an inert organic solvent, for example a halogenated hydrocarbon, e.g. dichloromethane, at a temperature between 15° and 75° C., preferably between 20° and 40° C.

Compounds of formula XIII wherein R² represents a tert-butyldiphenylsilyl group or a trialkylsilyl group of formula III (wherein R³, R⁴ and R⁵ are as hereinbefore defined) may be prepared by the reaction of compounds of formula XII with 1,3-di-tert-butyl-1,1,3,3-tetraphenyldisilazane or with a hexaalkyldisilazane of the general formula:

$$R^5R^4R^3Si-NH-SiR^3R^4R^5 \qquad XVII$$

(wherein R³, R⁴ and R⁵ are as hereinbefore defined) in the presence of tert-butyldiphenylchlorosilane or of a trialkylchlorosilane of the formula R⁵R⁴R³SiCl (R³, R⁴ and R⁵ being as hereinbefore defined) respectively, or of hydrogen chloride gas, under anhydrous conditions, for example in dry tetrahydrofuran as solvent.

Compounds of formula XII may be prepared by the esterification of compounds of formula XI by the application or adaptation of known methods for the esterification of carboxylic acids, for example by reaction with the corresponding diazoalkane of the general formula:

$$R^9=N_2 \qquad XVIII$$

(wherein R⁹ represents an alkylidene group, preferably containing from 1 to 4 carbon atoms, preferably the methylidene group CH₂) in an ether, e.g. diethyl ether.

Compounds of formula XI may be prepared by the reduction of compounds of formula X for example by means of an alkali metal borohydride, for example sodium borohydride or potassium borohydride or lithium tri-sec-butyl borohydride.

Compounds of formula X may be prepared by the oxidation of compounds of formula IX for example by means of a mixture of chromium trioxide and concentrated sulphuric acid in dimethylformamide.

Compounds of formula IX may be prepared by the acid hydrolysis of compounds of formula VIII in conditions similar to those hereinbefore described for the preparation of compounds of formula I from compounds of formula II.

Compounds of formula VIII may be prepared from compounds of formula VII by reaction with compounds of the general formula:

$$(R^{10})_3P=CHCOCH_2R^1 \qquad XIX$$

(wherein $R^1$ is as hereinbefore defined and $R^{10}$ represents a phenyl or n-butyl group) in the presence of tetrahydrofuran and at a temperature between 20° and 100° C. or in the presence of hexamethylphosphotriamide as solvent at between 95° and 100° C., or, preferably, with compounds of the general formula:

$$(R^{11}O)_2P(O)CH_2COCH_2R^1 \qquad XX$$

(wherein $R^1$ is as hereinbefore defined and $R^{11}$ represents an alkyl group of from 1 to 4 carbon atoms, preferably a methyl group) in the presence of a base, preferably sodium hydride, in an ethereal solvent, e.g. tetrahydrofuran.

Compounds of formula VII may be prepared by reaction of compounds of formula VI with 9-borabicyclo[3,3,1]nonane in dry tetrahydrofuran at a temperature between room temperature and the reflux temperature, followed by carbon monoxide in the presence of lithium aluminium tri-t-butoxyhydride in oxygen-free, dry, tetrahydrofuran at below room temperature, e.g. −35° C.

Compounds of formula VI may be prepared from compounds of formula V in a manner similar to that hereinbefore described for the preparation of compounds of formula XIII from compounds of formula XII.

By the term "pharmaceutically acceptable salts", as used in this specification, is meant salts the cations of which are relatively innocuous to the animal organism when used in therapeutic doses so that the beneficial pharmacological properties of the parent carboxylic acid compound of general formula I are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts.

As well as being useful in themselves as pharmaceutically useful compounds, salts of compounds of formula I are useful for the purpose of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid.

The aforementioned esters of the compounds of formula I, which constitute a feature of the present invention, are preferably compounds of the general formula:

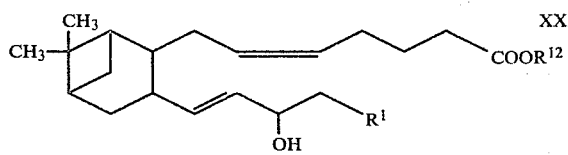
XXI

[wherein $R^1$ is as hereinbefore defined and $R^{12}$ represents a straight- or branched-chain alkyl group containing from 1 to 12 (preferably from 1 to 4 or from 7 to 12) carbon atoms], and they are prepared by the esterification of the corresponding carboxylic acids of formula I by the application of adaptation of known methods for the esterification of carboxylic acids.

Thus, the esterification can be carried out by reaction of the carboxylic acid with (i) an alcohol of the general formula:

$$R^{12}OH \qquad XXII$$

(wherein $R^{12}$ is as hereinbefore defined) an excess of which may be employed as solvent medium, in the presence of an inorganic acid, e.g. hydrochloric acid or sulphuric acid, preferably at a temperature between 50° and 160° C., and advantageously at the reflux temperature of the reaction mixture, or (ii) in the case where the desired ester is a compound of formula XXI wherein $R^{12}$ represents a group of the formula —$CHR^{13}R^{14}$ (wherein the symbols $R^{13}$ and $R^{14}$ are identical or different and each represents an alkyl group or, preferably, a hydrogen atom, the total number of carbon atoms in the group —$CHR^{13}R^{14}$ being at most 12), by reaction with a diazoalkane of the general formula:

$$R^{13}R^{14}C{=}N_2 \qquad XXIII$$

(wherein $R^{13}$ and $R^{14}$ are as hereinbefore defined) in an inert organic solvent, preferably a dialkyl ether (e.g. diethyl ether), preferably at ambient temperature.

Alternatively, a silver salt of a carboxylic acid of formula I can be reacted with an alkyl halide of the general formula:

$$R^{12}Z^1 \qquad XXIV$$

(wherein $Z^1$ represents a halogen atom and $R^{12}$ is as hereinbefore defined), optionally in the presence of an inert organic solvent, for example an aromatic hydrocarbon (e.g. benzene), at elevated temperature, for example at between 40° and 110° C., and advantageously at the reflux temperature of the reaction mixture.

It is to be understood that where, in this specification, reference is made to compounds of formula I, it is intended to refer also, where the context so permits, to the said salts and esters of the compounds of formula I.

As will be readily appreciated by those skilled in the art, the isomeric forms of the compounds of the invention arising from the aforementioned centres of chirality may be separated by the application or adaptation of known methods, for example diasteroisomeric forms may be separated by chromatography using selective adsorption from solution or from the vapour phase onto suitable adsorbents.

Similarly, diastereoisomeric forms of intermediates described in this specification may be separated by the application or adaptation of known methods.

Compounds of formula II and XI are new and as such constitute further features of the present invention.

The following Examples illustrate the preparation of the new compounds of formula I of the present invention, and the Reference Examples illustrate the preparation of intermediates.

EXAMPLE 1

7-{3-[3-(2-Tetrahydropyranyloxy)oct-trans-1-enyl]-6,6-dimethylbicyclo[3,1,1]hept-2-yl}hept-cis-5-enoic acid (60 mg; prepared as described hereinafter in Reference Example 1) was mixed with a mixture (2 ml) of water, acetic acid and tetrahydrofuran (35:65:10 by volume), and the mixture obtained was stirred at a temperature between 40° C. and 45° C. for 3 hours. The reaction mixture was cooled and then diluted with water and diethyl ether. The organic phase was washed several times with water, until a pH between 5 and 6 was obtained, and was then dried over sodium sulphate and evaporated in vacuo to give a residue (35 mg). This residue was subjected to thin layer chromatography on silica gel, using a mixture of diethyl ether, ethyl acetate and hexane (3:1:1 by volume) as eluant, to give 7-{3-(3-hydroxyoct-trans-1-enyl)-6,6-dimethylbicyclo[3,1,1]hept-2-yl}hept-cis-5-enoic acid (18 mg) [$\nu_{max}$ (liquid film): 980, 1715, 2650, 2920 and 3350 cm$^{-1}$. Nuclear magnetic resonance spectrum (N.M.R) (10% w/v solution in deuterochloroform): broad singlet at 7.2$\delta$, broad multiplets at 5.3$\delta$, 4.1$\delta$, 1.5$\delta$. Mass spectrum peaks at 376, 358, 305 and 231].

This material was thought to be one of the isomers 7-{(1S,2R,3R,5S)-3-[3-(R or S)-hydroxyoct-trans-1-enyl]-6,6-dimethylbicyclo[3,1,1,]hept-2-yl}-hept-cis-5-enoic acid, probably 7-{(1S,2R,3R,5S)-3-(3S-hydroxyoct-trans-1-enyl)-6,6-dimethylbicyclo[3,1,1]-hept-2-yl}hept-cis-5-enoic acid.

EXAMPLE 2

By proceeding in a manner similar to that hereinbefore described in Example 1, but replacing the starting material by component 12C of 7-{3-[3-(2-tetrahydropyranyloxy)oct-trans-1-enyl]-6,6-dimethylbicyclo[3,1,1]hept-2-yl}hept-cis-5-enoic acid, prepared as described hereinafter in Reference Example 12, there was prepared 7-}3-(3-hydroxyoct-trans-1-enyl)-6,6-dimethylbicyclo[3,1,1]hept-2-yl}hept-cis-5-enoic acid, thought to be the isomer 7-}(1S,2R,3R,5S)-3-(3S-hydroxyoct-trans-1-enyl)-6,6-dimethylbicyclo[3,1,1]-hept-2-yl}hept-cis-5-enoic acid.

EXAMPLE 3

By proceeding in a manner similar to that hereinbefore described in Example 1, but replacing the starting material by component 13D of 7-{3-[3-(2-tetrahydropyranyloxy)oct-trans-1-enyl]-6,6-dimethylbicyclo[3,1,1]hept-2-yl}hept-cis-5-enoic acid, prepared as described hereinafter in Reference Example 13, there was prepared 7-{3-(3-hydroxyoct-trans-1-enyl)-6,6-dimethylbicyclo[3,1,1]hept-2-yl}hept-cis-5-enoic acid, thought to be the isomer 7-{(1S,2R,3R,5S)-3-(3R-hydroxyoct-trans-1-enyl)-6,6-dimethylbicyclo-[3,1,1]hept-2-yl}hept-cis-5-enoic acid.

REFERENCE EXAMPLE 1

A 50% w/w suspension of sodium hydride in oil (41 mg) was washed twice with dry pentane and was then suspended in dry dimethyl sulphoxide (2 ml). The resulting mixture was heated at a temperature between 65° and 70° C., under a nitrogen atmosphere, with stirring, until the evolution of hydrogen had ceased. The mixture was then cooled to 10° C. and treated, dropwise, with a solution of (4-carboxybutyl)triphenylphosphonium bromide (0.25 g) in dry dimethyl sulphoxide (2 ml). The mixture was stirred at room temperature for 15 minutes, during which time a deep cherry red colouration appeared, and was then treated with a solution of {3-[3-(2-tetrahydropyranyloxy)oct-trans-1-enyl]-6,6-dimethylbicyclo[3,1,1]hept-2-yl}acetaldehyde (70 mg; prepared as described hereinafter in Reference Example 2) in dry dimethyl sulphoxide (2 ml), in one portion, and the reaction mixture was stirred for 3 hours under a nitrogen atmosphere. The reaction mixture was then added to crushed ice with vigorous stirring, and the resulting aqueous solution was washed with a mixture of diethyl ether and ethyl acetate (1:1 v/v), was adjusted to pH 4 by treatment with hydrochloric acid (2 N) and was then extracted with diethyl ether. The ethereal extract was dried over sodium sulphate and evaporated, to give crude 7-{3-[3-(2-tetrahydropyranyloxy)oct-trans-1-enyl]-6,6-dimethylbicyclo[3,1,1]hept-2-yl}hept-cis-5-enoic acid (60 mg), pure enough for use as a starting material in Example 1. [$\nu_{max}$ (liquid film): 985, 1028, 1730, 2940, 3040 and 3440 cm$^{-1}$].

REFERENCE EXAMPLE 2

A suspension of pyridinium chlorochromate (203 mg) and sodium acetate (14.6 mg) in dry methylene chloride (6 ml) was treated, all at once, with a solution of 2-{3-[3-(2-tetrahydropyranyloxy)oct-trans-1-enyl]-6,6-dimethylbicyclo[3,1,1]hept-2-yl}ethanol (227 mg; "isomer A" prepared as described hereinafter in Reference Example 3) in dry methylene chloride (6 ml). The mixture was stirred for 90 minutes and was then filtered through diatomaceous earth and concentrated in vacuo. The resulting oil (130 mg) was purified by thin layer chromatography on silica gel, using a mixture of diethyl ether, ethyl acetate and hexane (3:1:1 by volume) as eluant, to give {3-[3-(2-tetrahydropyranyloxy)oct-trans-1-enyl]-6,6-dimethylbicyclo[3,1,1]hept-2-yl}acetaldehyde (80 mg). [$\nu_{max}$ (liquid film): 985, 1028, 1670, 1730, 2700, 2860, 2940 cm$^{-1}$].

REFERENCE EXAMPLE 3

A stirred suspension of lithium aluminium hydride (100 mg) in dry tetrahydrofuran (1.1 ml) was treated with a solution of methyl {3-[3-(2-tetrahydropyranyloxy)oct-trans-1-enyl]-6,6-dimethylbicyclo[3,1,1]hept-2-yl}acetate (100 mg; prepared as described hereinafter in Reference Example 4) in dry tetrahydrofuran (1.1 ml) and the mixture was stirred for 4.5 hours. The mixture was then treated carefully with water (5 ml) and extracted three times with diethyl ether. The ethereal extracts were combined, dried over sodium sulphate, and evaporated in vacuo, to give 2-{3-[3-(2-tetrahydropyranyloxy)oct-trans-1-enyl]-6,6-dimethylbicyclo[3,1,1]hept-2-yl}ethanol (82 mg) [$\nu_{max}$ (liquid film): 820, 870, 910, 980–990, 1022, 1203, 2940, 3440 cm$^{-1}$. N.M.R. (10% w/v solution in deuterochloroform); broad doublets at 5.48$\delta$ (J=7 Hertz) and 5.23$\delta$ (J=7 Hertz), broad multiplets at 4.73$\delta$, 3.75$\delta$ and 1.5$\delta$].

Qualitative thin layer chromatography on silica gel, using a mixture of diethyl ether, ethyl acetate and hexane (3:1:1 by volume) as eluant, showed two spots of equal intensity. These were thought to indicate that two diastereoisomers had been separated. These were separated by preparative thin layer chromatography into the two components, designated as isomer A and isomer B, with isomer A having a lower Rf value than that of isomer B.

Isomer A was used for the next stage (Reference Example 2).

REFERENCE EXAMPLE 4

A stirred solution of methyl {3-(3-hydroxyoct-trans-1-enyl)-6,6-dimethylbicyclo[3,1,1]hept-2-yl}acetate (160 mg; prepared as described hereinafter in Reference Example 5) in dry dichloromethane (1.5 ml) was treated with concentrated hydrochloric acid (1 drop) followed by 2,3-dihydropyran (80 mg), dropwise. The mixture was then stirred at 40° C. for 3 hours, maintaining the pH at 1 by the addition, as required, of one or more further small quantities of concentrated hydrochloric acid. The mixture was then added to ice-cold aqueous sodium hydroxide solution (2 N; 0.25 ml), with vigorous stirring, and was then extracted with diethyl ether. The ether extract was washed with water, dried over sodium sulphate and concentrated in vacuo. The resulting residue (195 mg) was purified by thin layer chromatography on silica gel, using a mixture of diethyl ether, ethyl acetate and hexane (3:1:1 by volume) as eluant, to give methyl {3-[3-(2-tetrahydropyranyloxy)oct-trans-1-enyl]-6,6-dimethylbicyclo[3,1,1]hept-2-yl}acetate (120 mg). [$\nu_{max}$ (liquid film): 980, 1020, 1740 cm$^{-1}$. N.M.R. (10% w/v solution in deuterochloroform): broad multiplets at 5.35$\delta$, 4.75$\delta$, 3.5$\delta$ and 1.75$\delta$, singlet at 3.7$\delta$].

REFERENCE EXAMPLE 5

A solution of {3-(3-hydroxyoct-trans-1-enyl)-6,6-dimethylbicyclo[3,1,1]hept-2-yl}acetic acid (220 mg; the mixture of diastereoisomers prepared as described hereinafter in Reference Example 6) in diethyl ether (5 ml) was treated gradually with a solution of diazomethane in diethyl ether until the characteristic yellow colouration of the diazomethane remained. The mixture was left to stand for 18 hours and was then filtered. The filtrate was evaporated to dryness to give methyl {3-(3-hydroxyoct-trans-1-enyl)-6,6-dimethylbicyclo[3,1,1]hept-2-yl}acetate (200 mg). [$\nu_{max}$ (liquid film): 970, 1740, 3450 cm$^{-1}$].

REFERENCE EXAMPLE 6

A stirred solution of L-Selectride (lithium tri-sec-butyl borohydride) in tetrahydrofuran (1 M; 3.92 ml) at −70° C. under nitrogen was treated dropwise with a solution of {6,6-dimethyl-3-(3-oxooct-trans-1-enyl)bicyclo[3,1,1]hept-2-yl}acetic acid (600 mg; prepared as described hereinafter in Reference Example 7) in dry tetrahydrofuran (2 ml), and the mixture was stirred for 30 minutes at −70° C. and then for 150 minutes at room temperature. The mixture was then cooled to 0° C. and treated with aqueous sodium hydroxide solution (3 N; 3 ml). The mixture was then carefully treated with aqueous hydrogen peroxide solution (30% w/w; 2 ml) and stirred for 30 minutes. The mixture was then diluted with water (15 ml), washed with diethyl ether, and acidified to pH 3 by treatment with hydrochloric acid (2 N). The mixture was then extracted twice with diethyl ether and the extracts were combined, dried over sodium sulphate and evaporated in vacuo, to give {3-(3-hydroxyoct-trans-1-enyl)-6,6-dimethylbicyclo[3,1,1]hept-2-yl}acetic acid (310 mg). [$\nu_{max}$ (liquid film): 970, 1710, 3215 cm$^{-1}$; (KBr disc): 970, 1690, 2610, 3220 cm$^{-1}$. N.M.R. (10% w/v solution in deuterochloroform): broad singlet (exchangeable with D$_2$O) at 6.13$\delta$, broad multiplets at 5.44$\delta$, 4.05$\delta$, 1.7$\delta$].

Qualitative thin layer chromatography on silica gel, using a mixture of diethyl ether, ethyl acetate and hexane (3:1:1 by volume) as eluant, showed two spots of equal intensity. These were thought to indicate that two diastereoisomers had been formed by the conversion of the carbonyl group in the starting material into a hydroxymethylene group containing a new centre of chirality.

After the product had been left standing for 24 hours, some of it was found to have solidified. A sample of this solid was removed and examined by thin layer chromatography, using the same eluant system as had been used previously, and only one spot appeared. The I.R and N.M.R. spectra of the solid were similar to those displayed by the mixture, and it was concluded that the solid was a single diastereoisomer of {3-[3-hydroxyoct-trans-1-enyl]-6,6-dimethylbicyclo[3,1,1]hept-2-yl}acetic acid. Its melting point was 103°–104° C.

REFERENCE EXAMPLE 7

A stirred solution of 1{2-(2-hydroxyethyl)-6,6-dimethylbicyclo[3,1,1]hept-3-yl}oct-trans-1-en-3-one (700 mg; prepared as described hereinafter in Reference Example 8) in dry dimethylformamide (14.5 ml) at 5° C. was treated with dried chromium trioxide (1.84 g), portionwise, during 30 minutes. The mixture was stirred for a further period of 30 minutes, and then, at 5° C., was treated dropwise with a solution of concentrated sulphuric acid (1.42 ml) in dry dimethylformamide (45 ml). The mixture was stirred for 90 minutes and was then diluted with diethyl ether (40 ml) and decanted from resinous by-products. The ethereal solution was washed three times with water, dried over sodium sulphate, and concentrated in vacuo, to give {6,6-dimethyl-3-(3-oxooct-trans-1-enyl)bicyclo[3,1,1]hept-2-yl}acetic acid (640 mg). [$\nu_{max}$ (liquid film): 988, 1630, 1680, 1712 cm$^{-1}$].

REFERENCE EXAMPLE 8

A mixture of 1-{2-[2-(2-tetrahydropyranyloxy)ethyl]-6,6-dimethylbicyclo[3,1,1]hept-3-yl}oct-trans-1-en-3-one (900 mg; prepared as described hereinafter in Reference Example 9), acetic acid (18 ml), water (9 ml) and tetrahydrofuran (1.8 ml) was stirred at 45° C. for 4 hours. The mixture was then cooled, diluted with diethyl ether (40 ml) and with water (30 ml) and separated. The organic phase was washed three times with water and once with saturated aqueous sodium bicarbonate solution, dried over sodium sulphate, and concentrated in vacuo, to give 1-{2-(2-hydroxyethyl)-6,6-dimethylbicyclo[3,1,1]hept-3-yl}oct-trans-1-en-3-one (670 mg), in the form of a pale yellow oil. [$\nu_{max}$ (liquid film): 980, 1030, 1060, 1622, 1670, 3450 cm$^{-1}$].

REFERENCE EXAMPLE 9

A stirred suspension of sodium hydride (120 mg) in dry tetrahydrofuran (75 ml) under nitrogen was treated with a solution of dimethyl 2-oxoheptylphosphonate (1.0 g) in dry tetrahydrofuran (30 ml), and the mixture was stirred for 90 minutes, until evolution of hydrogen ceased. The mixture was then treated with a solution of freshly prepared 2-[2-(2-tetrahydropyranyloxy)ethyl]-6,6-dimethylbicyclo[3,1,1]heptane-3-carbaldehyde (1.2 g; prepared as described in Reference Example 10) in dry tetrahydrofuran (30 ml), and stirring was continued for a further period of 150 minutes. The mixture was then concentrated in vacuo, diluted with diethyl ether (100 ml), washed three times with water, dried over sodium sulphate, and concentrated in vacuo. The resulting residue (1.3 g) was purified by chromatography on a column of silica (45 g), using a mixture of diethyl ether and hexane (1:5 v/v) as the eluant, to give 1-{2-[2-(2-tetrahydropyranyloxy)ethyl]-6,6-dimethylbicyclo[3,1,1]hept-3-yl}oct-trans-1-en-3-one (0.68 g), in the form of a pale yellow oil. [$\nu_{max}$ (liquid film): 978, 988, 1032, 1622, 1675, 1695 cm$^{-1}$. N.M.R. (10% w/v solution in deuterochloroform): doublet of doublets at 6.75$\delta$ (J=7 Hertz and 15.5 Hertz), doublet at 6.0$\delta$ (J=15.5 Hertz), broad multiplets at 4.5$\delta$, 3.6$\delta$ and 1.6$\delta$. $\lambda_{max}$ 230, $\epsilon$14700. C$_{24}$H$_{40}$O$_3$ requires: C,76.55% H,10.71%; found: C,76.5% H,10.8%.]

REFERENCE EXAMPLE 10

A stirred solution of 2-{(1R,5S)-6,6-dimethylbicyclo[3,1,1]hept-2-en-2-yl}ethyl tetrahydropyran-2-yl ether (12 g) in dry tetrahydrofuran (40 ml) was treated dropwise, under nitrogen and at room temperature, with a solution of 9-borabicyclo[3,3,1]nonane (6.1 g) in dry tetrahydrofuran (100 ml). There occurred a slight evolution of a gas. The mixture was stirred for 30 minutes at room temperature and was then heated at reflux for 18 hours. The reaction vessel was then flushed out with carbon monoxide gas. The mixture was cooled to −35° C. and treated dropwise with a solution of lithium aluminium tri-t-butoxyhydride (12.7 g) in tetrahydrofuran (dry and freed from oxygen; 50 ml) during 45 minutes. The mixture was stirred for a further period of 90 minutes at −35° C. and was then allowed to warm to room temperature, meanwhile maintaining a slight positive pressure of carbon monoxide. The mixture was then treated with a pH 7 buffer [a solution of dipotassium hydrogen phosphate (264 mmoles) and sodium dihydrogen phosphate (264 mmoles) in water (120 ml)] followed, dropwise and with cooling by means of an external ice-bath, by aqueous hydrogen peroxide solution (30% w/w; 22 ml). The mixture was stirred for 30 minutes and was then diluted with saturated aqueous sodium chloride solution (100 ml). The organic layer was separated off, washed with a further quantity of saturated aqueous sodium chloride solution (100 ml), dried over sodium sulphate and concentrated in vacuo, to give a milky white oil (23 g). Purification by column chromatography on silica, using a mixture of diethyl ether and hexane (1:5 v/v), gave 2-[2-(2-tetrahydropyranyloxy)ethyl]-6,6-dimethylbicyclo[3,1,1]heptane-3-carbaldehyde (3.5 g). [$\nu_{max}$ (Liquid film): 988, 1005, 1728, 2600 cm$^{-1}$]. This product was rather unstable and was used immediately in Reference Example 9.

REFERENCE EXAMPLE 11

A solution of 2-{(1R,5S)-6,6-dimethylbicyclo[3,1,1]hept-2-en-2-yl}ethanol (61.6 g) in a minimum of dichloromethane (20 ml) was acidified by treatment with concentrated hydrochloric acid (2 drops). The solution was then treated with 2,3-dihydropyran (56 g), dropwise, at such a rate that the temperature rose to 60° C. and remained at 60° C. During the addition of the 2,3-dihydropyran the acidic nature of the mixture was maintained by the addition of one or more further small quantities of concentrated hydrochloric acid. The mixture was stirred at 60° C. for a further period of 3 hours, and was then added dropwise to a vigorously stirred, ice-cooled, aqueous sodium hydroxide solution (2 N; 91 ml). The resulting mixture was extracted with diethyl ether and the ethereal extract was dried over sodium sulphate, and concentrated and distilled in vacuo, to give 2-{(1R,5S)-6,6-dimethylbicyclo[3,1,1]hept-2-en-2-yl}ethyl tetrahydropyran-2-yl ether (74 g), b.p. 160°-167° C./14 mmHg [$\nu_{max}$ (liquid film): 978, 998, 1038 cm$^{-1}$. N.M.R. (10% w/v solution in deuterochloroform): multiplets at 5.3δ, 4.55δ, 2.25δ, 1.6δ, broad multiplet at 3.6δ, singlets at 1.3δ, 0.83δ. C$_{16}$H$_{26}$O$_2$ requires C,76.75%; H,10.47%; found C,76.75%; H,10.6%].

REFERENCE EXAMPLE 12

A stirred suspension of (4-carboxybutyl)triphenylphosphonium bromide (0.95 g) in dry tetrahydrofuran (20 ml) under a nitrogen atmosphere was treated with a solution of potassium tert-butoxide (0.6 g) in dry tetrahydrofuran (14 ml), and stirring was continued for a further period of 30 minutes, during which the white suspension became a deep orange solution. This solution was then treated with a solution of component 14C of {3-[3-(2-tetrahydropyranyloxy)oct-trans-1-enyl]-6,6-dimethylbicyclo[3,1,1]hept-2-yl}acetaldehyde (0.2 g; prepared as described hereinafter in Reference Example 14) in dry tetrahydrofuran (4 ml). The mixture was stirred for one hour and was then treated with water (6 ml) and stirred for a further period of 30 minutes. The mixture was then agitated with diethyl ether and aqueous sodium carbonate solution (2 N). The aqueous phase was separated and acidified to pH 1 by treatment with hydrochloric acid, and it was then extracted with diethyl ether. The ethereal extract was dried over sodium sulphate and concentrated in vacuo to give 7-{3-(3-(2-tetrahydropyranyloxy)oct-trans-1-enyl]-6,6-dimethylbicyclo[3,1,1]hept-2-yl}hept-cis-5-enoic acid (0.2 g) in the form of an oil. This material was designated as component 12C and was thought to be the isomer 7-{(1S,2R,3R,5S)-3-[3S-(2-tetrahydropyranyloxy)oct-trans-1-enyl]-6,6-dimethylbicyclo[3,1,1]hept-2-yl}hept-cis-5-enoic acid.

REFERENCE EXAMPLE 13

By proceeding in a manner similar to that hereinbefore described in Reference Example 12, but replacing the starting material by component 15D of {3-[3-(2-tetrahydropyranyloxy)oct-trans-1-enyl]-6,6-dimethylbicyclo[3,1,1]hept-2-yl}acetaldehyde, prepared as described hereinafter in Reference Example 15, there was prepared 7-{3-[3-(2-tetrahydropyranyloxy)oct-trans-1-enyl]-6,6-dimethylbicyclo[3,1,1]hept-2-yl}hept-cis-5-enoic acid. This material was designated as component 13D and was thought to be the isomer 7-{(1S,2R,3R,5S)-3-[3R-(2-tetrahydropyranyloxy)oct-trans-1-enyl]-6,6-dimethylbicyclo[3,1,1]hept-2-yl}hept-cis-5-enoic acid.

REFERENCE EXAMPLE 14

By proceeding in a manner similar to that hereinbefore described successively in Reference Examples 5, 4, 3 and 2, but replacing the starting material used in Reference Example 5 by component 16C of {3-(3-hydroxyoct-trans-1-enyl)-6,6-dimethylbicyclo[3,1,1]hept-2-yl}acetic acid, prepared as described hereinafter in Reference Example 16, there was prepared {3-[3-(2-tetrahydropyranyloxy)oct-trans-1-enyl]-6,6-dimethylbicyclo[3,1,1]hept-2-yl}acetaldehyde. This material was designated as component 14C and was thought to be the isomer (1S,2R,3R,5S)-{3-[3S-(2-tetrahydropyranyloxy)oct-trans-1-enyl]-6,6-dimethylbicyclo[3,1,1]hept-2-yl}acetaldehyde.

REFERENCE EXAMPLE 15

By proceeding in a manner similar to that hereinbefore described in Reference Example 14, but replacing the starting material by component 16D of {3-(3-hydroxyoct-trans-1-enyl)-6,6-dimethylbicyclo[3,1,1]hept-2-yl}acetic acid, prepared as described hereinafter in Reference Example 16, there was prepared {3-[3-(2-tetrahydropyranyloxy)oct-trans-1-enyl]-6,6-dimethylbicyclo[3,1,1]hept-2-yl}acetaldehyde. This material was designated as component 15D and was thought to be the isomer (1S,2R,3R,5S)-{3-[3R-(2-tetrahydropyranyloxy)oct-trans-1-enyl]-6,6-dimethylbicyclo[3,1,1]hept-2-yl}acetaldehyde.

REFERENCE EXAMPLE 16

By proceeding in a manner similar to that hereinbefore described in Reference Example 6 but on a larger scale, there was again prepared {3-(3-hydroxyoct-trans-1-enyl)-6,6-dimethylbicyclo[3,1,1]-hept-2-yl}acetic acid as a mixture of two components and, as in Reference Example 6, one of the components crystallised out of the mixture. This was separated off (450 mg) and the remaining oil was subjected to chromatography on a column of silica gel, using a mixture of diethyl ether, ethyl acetate and hexane (3:1:1 by volume) as the eluant. There were thereby obtained three substances, viz. (i) a further quantity (600 mg) of the aforementioned readily crystallised component, (ii) a quantity (520 mg) of the other component, in the form of an oil, and (iii) a quantity (300 mg) of a mixture of the two components.

The readily crystallised component was designated as component 16C, and was thought to be the isomer (1S,2R,3R,5S)-{3-(3S-hydroxyoct-trans-1-enyl)-6,6-dimethylbicyclo[3,1,1]hept-2-yl}acetic acid.

The other component, obtained in the form of an oil, was designated as component 16D, and was thought to be the isomer (1S,2R,3R,5S)-{3-(3R-hydroxyoct-trans-1-enyl)-6,6-dimethylbicyclo[3,1,1]hept-2-yl}acetic acid.

The present invention includes within its scope pharmaceutical compositions which comprise at least one compound of formula I together with a pharmaceutical carrier or coating. In clinical practice the compounds of formula I will normally be administered orally, rectally, vaginally or parenterally.

Solid compositions for oral administration include compressed tablets, pills, dispersible powders, and granules.

Liquid compositions for oral administration include pharmaceutically-acceptable emulsions, solutions, suspensions, syrups and elixirs.

The compositions according to the invention, for oral administration, also include capsules of absorbable material such as gelatin containing one or more of the compounds of formula I.

Solid compositions for vaginal administration include pessaries.

Solid compositions for rectal administration include suppositories.

Preparations according to the invention for parenteral administration include sterile aqueous or non-aqueous solutions, suspensions or emulsions.

The compounds of formula I may alternatively be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. The active ingredients may also be administered orally by inhalation in the form of aerosols generated from self-propelling pharmaceutical compositions.

Methods of presentation of pharmaceutically active compounds are well known in the art and a suitable vehicle may be determined by the physician, pharmacist or veterinarian, depending upon such factors as the effect sought, the size, age, sex and condition of the patient and, for veterinary uses, species of the animal to be treated, and on the physical properties of the active compound. The compositions may also contain, as is usual in the art, such materials as solid or liquid diluents, wetting agents, preservatives, flavouring and colouring agents and the like.

The percentage of active ingredient in the compositions of the invention may be varied, it being necessary that it should constitute a proportion such that a suitable dosage for the therapeutic effect desired shall be obtained. Obviously several unit dosage forms may be administered at about the same time.

In general, the compositions should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult, the doses are generally, for example, between 0.1 and 10 mg by vaginal administration, between 0.0005 and 0.02 mg/kg body weight by intravenous administration, and between 0.01 and 1.0 mg/kg body weight orally. If necessary these doses may be repeated as and when required.

The following Examples illustrate pharmaceutical compositions according to the invention.

EXAMPLE 4

7-{(1S,2R,3R,5S)-3-[3-(R or S)-Hydroxyoct-trans-1-enyl]-6,6-dimethylbicyclo[3,1,1]hept-2-yl}-hept-cis-5-enoic acid (0.5 mg) was dissolved in ethanol (1 ml) and the solution obtained was added to an aqueous solution (12 ml) containing sodium carbonate (5 mg). Aqueous sodium chloride solution (0.9% w/v; 2 ml) was then added to give a final volume of 15 ml. The solution was then sterilised by passage through a bacteria-retaining filter and placed in 1.5 ml portions in 5 ml ampoules, to give 0.05 mg of the active compound (in the form of its sodium salt) per ampoule. The contents of the ampoules were freeze-dried and the ampoules sealed. Dissolution of the contents of an ampoule in a suitable volume, e.g. 2 ml of sterile water or physiological saline gave a solution ready for administration by injection.

EXAMPLE 5

7-{(1S,2R,3R,5S)-3-[3-(R or S)-Hydroxyoct-trans-1-enyl]-6,6-dimethylbicyclo[3,1,1]hept-2-yl}-hept-cis-5-enoic acid, (10 mg) was dissolved in ethanol (10 ml), mixed with mannitol (18.5 g), sieved through a 30-mesh sieve, dried at 30° C. for 90 minutes and again sieved through a 30-mesh sieve. Aerosil (microfine silica) (200 mg) was added and the powder obtained was machine filled into one hundred No. 2 hard gelatin capsules to give capsules each containing 0.1 mg of the active compound which, after the capsules are swallowed, is released into the stomach.

EXAMPLE 6

Witepsol S-58 (a pessary-base supplied by Dynamit Nobel A.G.) (99 mg) was melted at below 40° C. and there was then added to it 7-{(1S,2R,3R,5S)-3-[3-(R or S)-hydroxyoct-trans-1-enyl]-6,6-dimethylbicyclo[3,1,1-]hept-2-yl}hept-cis-5-enoic acid (1.0 mg). After mixing to form a suspension, the suspension was poured into a pessary mould and cooled until the suspension became solid. There was thus obtained a pessary suitable for vaginal administration.

By proceeding in a manner similar to that described in Example 4, Example 5 or Example 6, but replacing the compound of formula I by one or more of the other compounds of formula I, there may be prepared further pharmaceutical compositions.

We claim:

1. A compound of the formula:

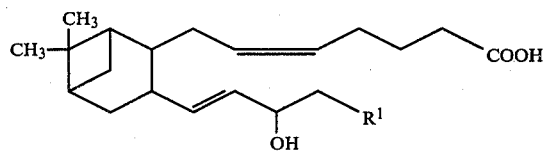

wherein $R^1$ represents a phenoxy or benzyl group, and pharmaceutically acceptable salts thereof, and alkyl esters thereof containing from 1 to 12 carbon atoms in the alkyl moiety which may be straight- or branched-chain.

2. A compound according to claim 1 wherein the esters are alkyl esters containing from 1 to 4 or from 7 to 12 carbon atoms in the alkyl moiety which may be straight- or branched-chain.

3. A compound according to claim 1 which has a configuration such that the side chains —$CH_2$—CH=CH—$(CH_2)_3$COOH and —CH=CH—CH(OH)—$CH_2$—$R^1$ are attached to the ring in the trans-configuration with respect to each other.

4. A compound according to claim 1 and conforming to the formula:

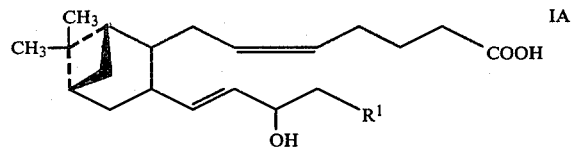

wherein $R^1$ is as defined in claim 1 and pharmaceutically acceptable salts thereof, and alkyl esters thereof containing from 1 to 12 carbon atoms in the alky moiety which may be straight- or branched-chain.

5. A compound according to claim 1 and conforming to the formula:

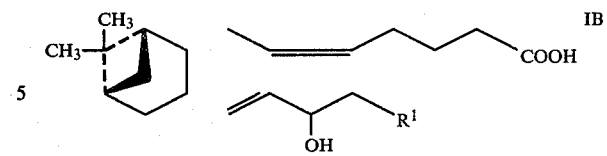

wherein $R^1$ is as defined in claim 1 and pharmaceutically acceptable salts thereof, and alkyl esters thereof containing from 1 to 12 atoms in the alkyl moiety which may be straight- or branched-chain.

6. A pharmaceutically acceptable salt of a compound claimed in claim 1.

7. An alkyl ester of a compound claimed in claim 1 containing from 1 to 12 carbon atoms in the alkyl moiety which may be straight- or branched-chain.

8. A pharmaceutical composition useful for modifying or synchronizing functions of the female mammalian reproductive system, and in the treatment or prevention of cardiovascular disease, which comprises at least one compound of formula I as defined in claim 1 or a pharmaceutically acceptable salt thereof, or alkyl ester thereof containing from 1 to 12 carbon atoms in the alkyl moiety which may be straight- or branched-chain, together with a pharmaceutical carrier or coating.

9. A compound of formula:

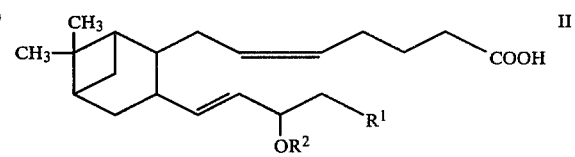

wherein $R^1$ represents phenoxy or benzyl and $R^2$ is a 2-tetrahydropyranyl group unsubstituted or substituted by at least one straight- or branched-chain alkyl group containing from 1 to 4 carbon atoms, or a 2-tetrahydrofuranyl group, or a tert-butyldiphenylsilyl group or a trialkylsilyl group of the formula:

—$SiR^3R^4R^5$ wherein $R^3$ and $R^4$, which may be the same or different, each represent a methyl or ethyl group and $R^5$ represents a straight- or branched-chain alkyl group containing from 1 to 4 carbon atoms, or a 1-alkoxyalkyl group of the formula:

—$CH(CH_2R^6)OR^7$ wherein $R^6$ represents a hydrogen atom or a straight- or branched-chain alkyl group containing from 1 to 4 carbon atoms and $R^7$ represents a straight- or branched-chain alkyl group containing from 1 to 4 carbon atoms.

* * * * *